Nov. 2, 1954 H. M. EDDIE Plant Pat. 1,314
ROSE PLANT
Filed Sept. 21, 1953 2 Sheets-Sheet 1
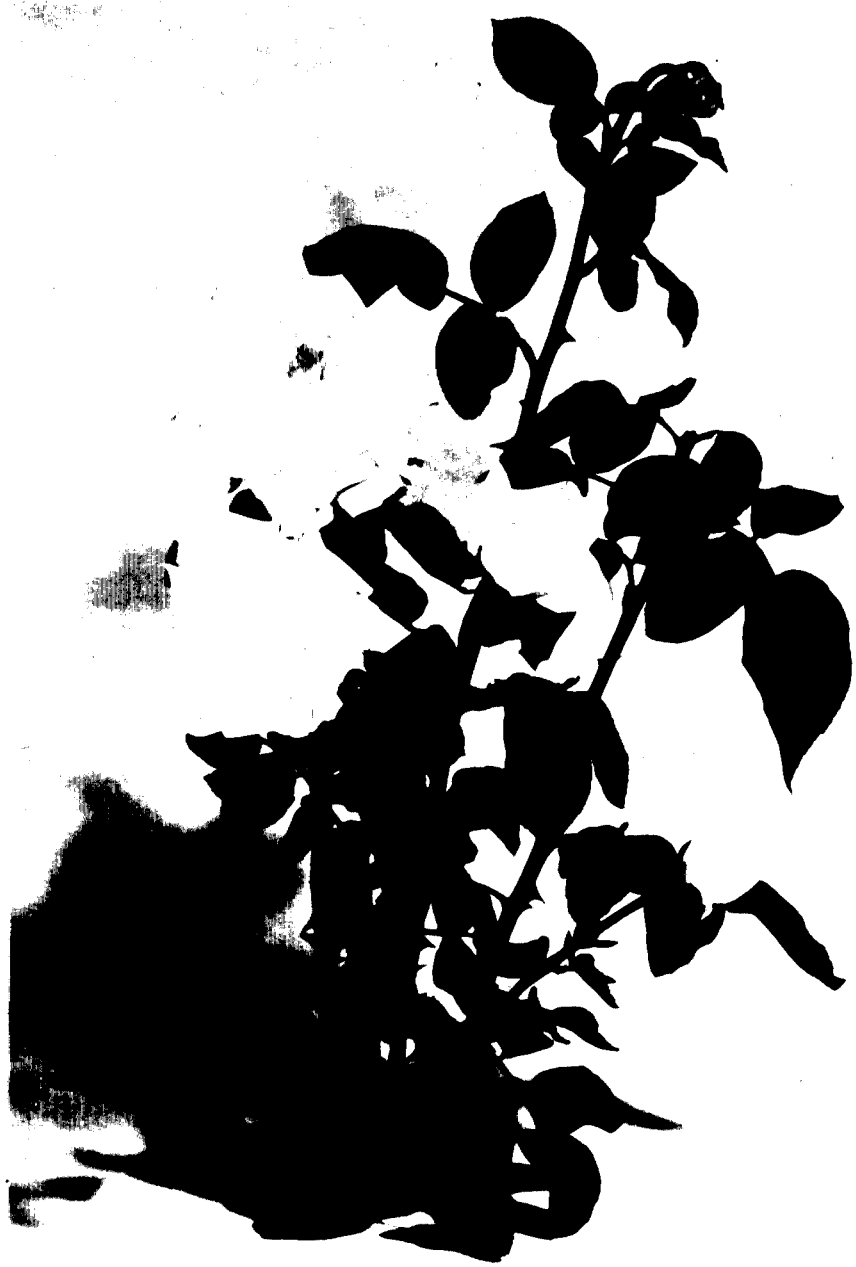
Inventor.
H. M. Eddie, Deceased,
By: J. H. Eddie,
Executor,
By: Robb & Robb, Attys.

Nov. 2, 1954 H. M. EDDIE Plant Pat. 1,314
ROSE PLANT
Filed Sept. 21, 1953 2 Sheets-Sheet 2
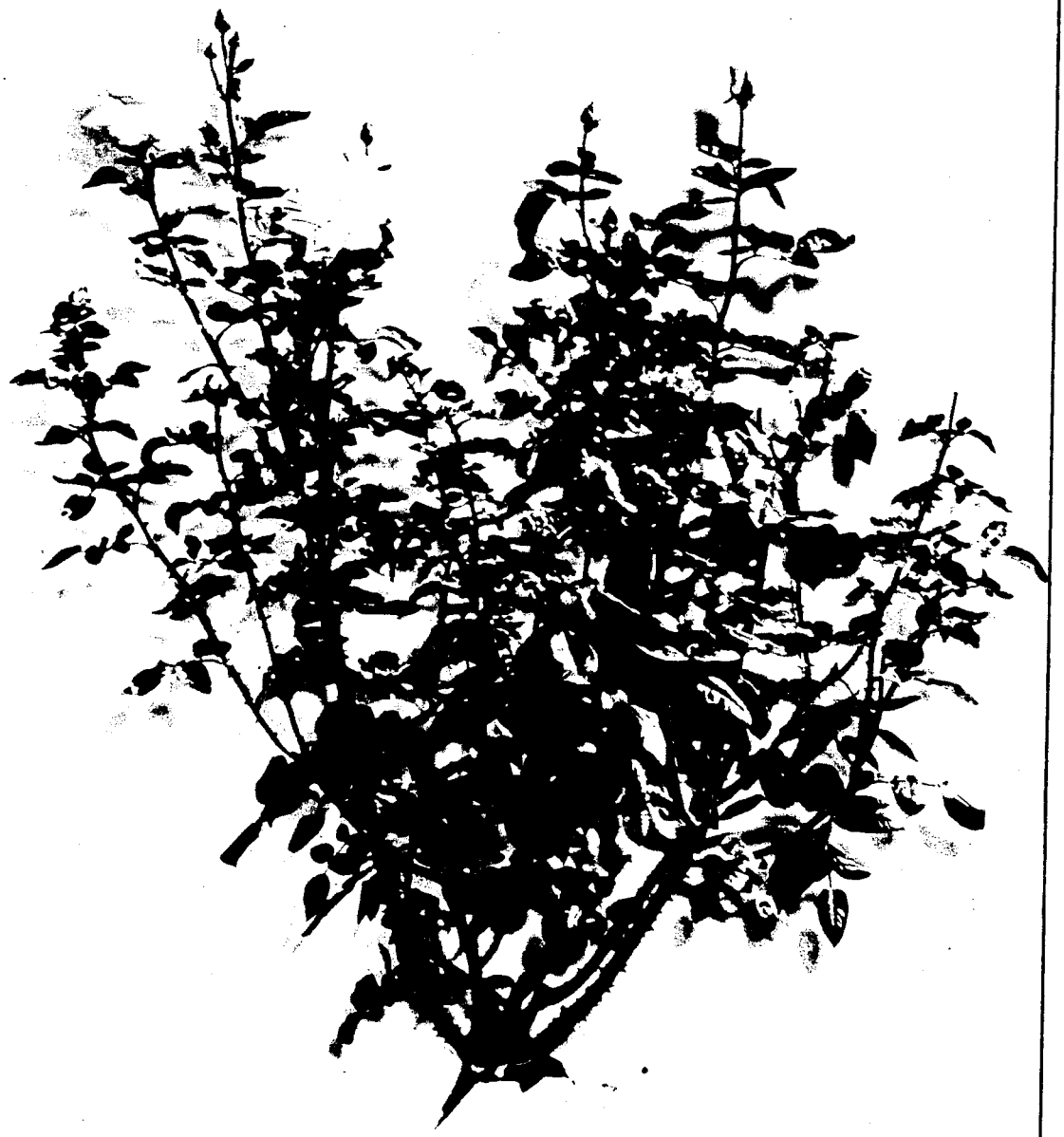
Inventor.
H. M. Eddie, Deceased
By: J. H. Eddie,
Executor,
By: Robb & Robb, attys.

United States Patent Office

Plant Pat. 1,314
Patented Nov. 2, 1954

1,314

ROSE PLANT

Henry Matheson Eddie, deceased, late of Vancouver, British Columbia, Canada, by J. Henry Eddie, executor, Vancouver, British Columbia, Canada, assignor to Eldon Pinkeney Dering, doing business as Peterson & Dering, Scappoose, Oreg.

Application September 21, 1953, Serial No. 381,527

1 Claim. (Cl. 47—61)

The present invention relates to a new and distinct variety of rose plant of the hybrid tea class which was originated by crossing the variety known as "Phyllis Gold" (unpatented) with the variety known as "Pres. Herbert Hoover" (unpatented).

The primary objective in making this cross was to produce a new variety of rose plant characterized by an improvement in the form, color-stability and continuity of the blooms, and which is particularly adapted to the climatic environment of the Pacific Northwest geographical area of the United States.

This objective was fully achieved, as evidenced by the fact that the new variety is phenotypically characterized by the following unique combination of features:

(1) The vigorous, well-branched, moderately tall (4 feet or more), but well-formed bush;

(2) Flowers usually borne singly on long, straight stems, but frequently with 3 or 4 blooms per stem;

(3) Flowers of distinct and unique pigmentation and of exceptionally good color-stability and form in this color range, as hereinafter more particularly described;

(4) Adequate and continuous flowering habit throughout growing season; and (5) Excellent distribution of foliage for a plant of its proportion.

The new variety is definitely distinguished from its parents, as well as from all other varieties of its class. In comparison with its parents, the new variety has more petals per bloom and less variability in the number of petals than the flowers of "Phyllis Gold," and many more petals than the flowers of the pollen parent "Pres. Herbert Hoover." The blooms of "Phyllis Gold" do not open as cleanly in wet weather as do those of the new variety, and the new variety has more blooms than this parent, and the flowers are more full and more regular than those of either parent, particularly "Pres. Herbert Hoover." The persistent high center and general symmetry of the flower of my new variety are quite distinct from either parent, as well as from all other varieties in any comparable color range, while the color of the flowers of my new variety is less variable and more intense than the color of the flowers of "Phyllis Gold," and lacks the Orange coloration which is characteristic of the flowers of "Pres. Herbert Hoover," and also lacks the Carmine flush of the mature blooms of "Phyllis Gold" except in the tight bud stage. The mature foliage of the new variety is larger and darker in color than that of "Phyllis Gold," and somewhat larger and more elongate in form than the mature foliage of "Pres. Herbert Hoover." The young foliage of the new variety has less Red coloration than is present in the young foliage of "Pres. Herbert Hoover." In respect to its general plant habits, the new variety is a stronger grower and the growth is better distributed than in the plants of "Phyllis Gold," and the new variety is more compact than plants of "Pres. Herbert Hoover."

The general color of the flowers of the new variety is somewhat similar to that of the variety known as "Mme. Chiang Kai-shek" (Plant Patent No. 664), but the flowers of the new variety are easily distinguished from that variety by virtue of the greater number of petals in the flowers of the new variety, their more formal and high-centered form, and their greater stability of coloration.

Asexual reproduction of the new variety by budding at Vancouver, British Columbia, shows that the foregoing characteristics and distinctions of the new variety come true to form and are established and transmitted through succeeding propagations.

The accompanying illustrations show typical specimens of the new variety, one of said illustrations depicting in color typical flowers, foliage and stems in different stages of development, while the other illustration depicts a specimen plant of the new variety in black-an-white and shows the general form of the plant.

The following is a detailed description of the new variety, with color terminology in accordance with Robert F. Wilson's Horticultural Colour Chart, except where general color terms of ordinary dictionary significance are obvious:

Type: Outdoor bush; seedling; for garden decoration and for cut flowers.
Class: Hybrid tea.
Breeding: Seedling.
*Seed parent.*—"Phyllis Gold."
*Pollen parent.*—"Pres. Herbert Hoover."
Propagation: Holds its distinguishing characteristics through succeeding propagations by budding.

(The following observations were made from specimens of the new variety as grown at Portland, Oregon.)

*Flower*

Flowers borne: Usually singly, but sometimes as many as 5 per stem; on long, strong stems.
Quantity of bloom: Free, outdoors.
Continuity: Continuous.
Fragrance: Moderate; slightly acrid.
Bud:
*Peduncle.*—Medium length (4 to 5 cm.); medium diameter (about 2 to 4 mm.); erect; almost smooth; with few light Yellow prickles and few gland-tipped cilia.
*Color.*—Between Lettuce Green, Plate 861/1, page 176 and Scheele's Green, Plate 860/1, page 175.
*Before calyx breaks.*—Size—medium (about 16 x 30 mm.). Form—medium pointed; with foliaceous appendages on the margins of sepals; with slender, nearly entire foliaceous parts extending beyond the tip of the bud equal to less than ¼ of its length. Color—near Scheele's Green, Plate 860/1, page 175.
*As calyx breaks.*—Color—variable greenish-yellow; sometimes with localized Red flush.
*As first petal opens.*—Size—medium large. Form—medium long pointed. Color: outside—Empire Yellow, Plate 603, page 66; inside—Mimosa Yellow, Plate 602, page 143.
*Opening.*—Opens well under wide variation of environment.
Bloom:
*Size (when fully open).*—Large (9 to 15 cm.).
*Petalage.*—Double; from 56 to 73 petals, but average about 67; arranged regularly.
*Form.*—Very high-centered at first, becoming evenly open, but maintaining a high center well into maturity, or even into senescence; petals at first tightly clasping to cupped, with apical lateral margins rolled tightly outward forming an apical point; becoming loosely rolled outward at maturity.
Petals:
*Texture.*—Moderately thick and firm; inside satiny and somewhat leathery; outside satiny.
*Shape.*—Outside petal—orbicular-obovate; entire. Intermediate petal—obovate; entire. Inside petal—obovate; entire.

This description of a newly opened flower was made from a rose grown outdoors in the month of August at Portland, Oregon:

*Color.*—Outside petal: outer surface—Aureolin, Plate 3, page 3, shading to nearly white at apex; inner surface—Lemon Yellow, Plate 4, page 4, shading to nearly white at apex. Intermediate petal: outer surface—Empire Yellow, Plate 603, page 66, shading to Empire Yellow, Plate 603/2, page 66 at apex; inner surace—Mimosa Yellow, Plate 602, page 143, shading to Mimosa Yellow, Plate 602/2, page 143 at apex. Inside petal: outer surface—Empire Yellow, Plate 603, page 66, shading to Empire Yellow, Plate 603/1, page 66 at apex; inner surface—Mimosa Yellow, Plate 602, page 143, shading to Mimosa Yellow, Plate 602/1, page 143 at apex.

This description was made from a rose that was open for 3 days outdoors in the month of August at Portland, Oregon:

*Color.*—Outside petal: outer surface—Aureolin, Plate 3, page 3, shading to nearly white at apex; inner surface—Lemon Yellow, Plate 4, page 4, shading to nearly white at apex. Inside petal: outer surface—Lemon Yellow, Plate 4, page 4, shading to Primrose Yellow, Plate 601/3, page 65 at apex; inner surface—Lemon Yellow, Plate 4, page 4, shading to Primrose Yellow, Plate 601/2, page 65 at apex.

*General color effect.*—Newly opened flower—Lemon Yellow, Plate 4/2, page 4. 3-days open—from Mimosa Yellow, Plate 602/1, page 143 to Mimosa Yellow, Plate 602/2, page 143.

*Behavior.*—Petals drop off cleanly; fade to nearly white; rate of fading reaction increases with temperature and light intensity.

*Flower longevity.*—On outdoor bush—5 days in August. Cut flowers grown outdoors and kept at room temperatures—6 days in August.

*Reproductive organs*

Stamens: Moderate number (about 76); arranged regularly about pistils.

Filaments: Medium length (average 9 mm.); nearly all with anthers. Color—Indian Yellow, Plate 6, page 6, flushed with Red.

Anthers: Medium size (about 1.5 mm. x 2 to 3 mm.); nearly all open at the same time. Color—near Indian Yellow, Plate 6, page 6.

Pollen: Abundant. Color—variable yellow.

Pistils: Moderately numerous.

Styles: Normally even; medium length; thin; loosely bunched. Color—white at base, flushed with Cardinal Red, Plate 822/3, page 168 near apex.

Stigma: Somewhat translucent. Color—variable white to yellowish.

Ovaries: All enclosed in calyx.

Hips: Ovoid; moderately smooth; walls fleshy. Color—near Scheele's Green, Plate 860/1, page 175.

Sepals: Persistent; medium size (about 10 mm. x 27 mm.); spearshaped; curled. Color—near Scheele's Green, Plate 860, page 175, but frequently more blue toward apex.

Seeds: Few to moderate number; large.

*Plant*

Foliage:

*Leaves.*—Compound of 3 to 7 leaflets (usually 5); moderately abundant; medium-large to large (about 5.6 cm. x 9 cm.); heavy; semi-glossy.

*Leaflets.*—Broadly obovate with apex acute; base rounded to semi-cordate; margins simply serrate, but with some double serration detectable.

*Color.*—Mature: upper surface—between Spinach Green, Plate 0960, page 187 and Ivy Green, Plate 0001060, page 200; under surface—grey-green (Spinach Green, Plate 0960/3, page 187, is closest color in reference color chart). Young: upper surface—near Spinach Green, Plate 0960/1, page 187, but frequently flushed with lighter green to Lettuce Green, Plate 861, page 176; under surface—between Lettuce Green, Plate 861/2, page 176 and Scheele's Green, Plate 860/2, page 175, heavily washed with Purple Madder, Plate 1028, page 181 particularly on veins and margins.

*Rachis.*—Heavy. Upper side—grooved, with numerous glandular cilia on margins. Under side—moderately to lightly thorny, with few glandular cilia.

*Stipules.*—Medium length (20 to 30 mm.); medium width (up to 8 mm.); points moderately long (up to 10 mm.); turned out at an angle less than 45°.

*Disease resistance.*—Better than average resistance to mildew as determined from comparison with other varieties grown under comparable cultural conditions at Portland, Oregon.

Growth:

*Habit.*—Upright; moderately branched.

*Growth.*—Free.

*Canes.*—Heavy.

*Main stems.*—Color—dull green. Thorns—several; medium long (about 10 to 12 mm.); turned slightly downward; with medium oval base (about 7 x 3 mm.). Prickles—none. Hairs—none.

*Branches.*—Color—dull green. Thorns—several; medium long (about 9 to 11 mm.); hooked downward; with medium oval base (about 9 x 3 mm.). Prickles—none, but few gland-tipped cilia. Hairs—none.

*New shoots.*—Color—reddish green. Thorns—several; medium long (7 to 12 mm.); hooked downward; with medium oval base. Prickles—few; also few gland-tipped cilia. Hairs—none.

I claim:

A new and distinct variety of rose plant of the hybrid tea class, substantially as herein shown and described, characterized particularly as to novelty by its vigorous, well-branched, moderately tall and well-formed bush plant, by its good distribution of foliage for a plant of such proportion, by its habit of usually bearing flowers singly on long, straight stems, but frequently with three to four blooms per stem, by its adequate and continuous habit of bearing flowers throughout the growing season, and by the distinctive lemon yellow general color tonality of its flowers and their exceptionally good color-stability and form.

No references cited.